(12) United States Patent
Bunch et al.

(10) Patent No.: US 8,444,577 B2
(45) Date of Patent: May 21, 2013

(54) MEDICAL GUIDE WIRE

(75) Inventors: Tyler J. Bunch, Bloomington, IN (US); Valery Diamant, Katsrin (IL); Nadezda Yasko, Tomsk (RU)

(73) Assignee: Cook Medical Technologies LLC, Bloomington, IN (US)

( * ) Notice: Subject to any disclaimer, the term of this patent is extended or adjusted under 35 U.S.C. 154(b) by 537 days.

(21) Appl. No.: 12/348,715

(22) Filed: Jan. 5, 2009

(65) Prior Publication Data

US 2010/0174246 A1    Jul. 8, 2010

(51) Int. Cl.
*A61B 5/00* (2006.01)

(52) U.S. Cl.
USPC .......................................... 600/585

(58) Field of Classification Search
USPC ............... 600/102, 264, 585; 604/95.01, 264, 604/524, 525, 526, 528
See application file for complete search history.

(56) References Cited

U.S. PATENT DOCUMENTS

| | | | |
|---|---|---|---|
| 2,319,556 A | 5/1943 | Rhein et al. | |
| 3,301,393 A | 1/1967 | Regan, Jr. et al. | |
| 3,547,103 A | 12/1970 | Cook | |
| 4,003,369 A | 1/1977 | Heilman et al. | |
| 4,061,134 A | 12/1977 | Samuels et al. | |
| 4,215,703 A * | 8/1980 | Willson | 600/585 |
| 4,548,206 A | 10/1985 | Osborne | |
| 4,643,305 A | 2/1987 | De Roure Olivier | |
| 4,721,117 A | 1/1988 | Mar et al. | |
| 4,763,647 A | 8/1988 | Gambale | |
| 4,779,628 A | 10/1988 | Machek | |
| 4,846,186 A | 7/1989 | Box et al. | |
| 4,846,193 A | 7/1989 | Tremulis et al. | |
| 4,848,344 A | 7/1989 | Sos et al. | |
| 4,867,173 A | 9/1989 | Leoni | |
| 4,921,483 A | 5/1990 | Wijay et al. | |
| 4,925,445 A | 5/1990 | Sakamoto et al. | |

(Continued)

FOREIGN PATENT DOCUMENTS

EP    1 325 763 A2    7/2003
EP    1 464 358 A1    10/2004

(Continued)

OTHER PUBLICATIONS

International Preliminary Report on Patentability and Written Opinion of the International Searching Authority from PCT/US2010/020025.

(Continued)

*Primary Examiner* — Max Hindenburg
(74) *Attorney, Agent, or Firm* — Brinks Hofer Gilson & Lione

(57) ABSTRACT

A guide wire for guiding a medical device within a body lumen is described. The guide wire includes a proximal section, a distal section, and a mid section. The proximal section includes a proximal wire core tapered with contraction towards a proximal end of the proximal wire core. The distal section includes a distal wire core tapered with contraction towards a distal end of the distal wire core. The mid section includes a joint for joining the proximal wire core and the distal wire core. The guide wire also includes a safety wire extending along the mid section, and along at least parts of the proximal and distal sections. Moreover, the guide wire includes an outer tubing enveloping the overlapping joint and at least parts of the proximal and distal sections.

26 Claims, 10 Drawing Sheets

U.S. PATENT DOCUMENTS

| | | | | |
|---|---|---|---|---|
| 4,991,602 | A | 2/1991 | Amplatz et al. | |
| 5,084,022 | A | 1/1992 | Claude | |
| 5,120,308 | A | 6/1992 | Hess | |
| 5,125,416 | A | 6/1992 | Phillips | |
| 5,129,890 | A | 7/1992 | Bates et al. | |
| 5,188,621 | A * | 2/1993 | Samson | 604/528 |
| 5,209,735 | A | 5/1993 | Lazarus | |
| 5,213,111 | A | 5/1993 | Cook et al. | |
| 5,217,007 | A | 6/1993 | Ciaglia | |
| 5,242,759 | A | 9/1993 | Hall | |
| 5,243,996 | A | 9/1993 | Hall | |
| 5,251,640 | A | 10/1993 | Osborne | |
| 5,320,602 | A | 6/1994 | Karpiel | |
| 5,324,304 | A | 6/1994 | Rasmussen | |
| 5,354,623 | A | 10/1994 | Hall | |
| 5,363,847 | A | 11/1994 | Viera | |
| 5,380,292 | A | 1/1995 | Wilson | |
| 5,385,152 | A | 1/1995 | Abele et al. | |
| 5,421,349 | A | 6/1995 | Rodriguez et al. | |
| 5,533,985 | A * | 7/1996 | Wang | 604/264 |
| 5,568,865 | A | 10/1996 | Mase et al. | |
| 5,573,010 | A | 11/1996 | Pflugbeil | |
| 5,681,344 | A | 10/1997 | Kelly | |
| 5,725,534 | A | 3/1998 | Rasmussen | |
| 5,769,222 | A | 6/1998 | Banerian | |
| 5,769,830 | A | 6/1998 | Parker | |
| 5,772,609 | A | 6/1998 | Nguyen et al. | |
| 5,776,079 | A * | 7/1998 | Cope et al. | 600/585 |
| 5,924,998 | A | 7/1999 | Cornelius et al. | |
| 5,980,505 | A * | 11/1999 | Wilson | 604/525 |
| 6,001,068 | A | 12/1999 | Uchino et al. | |
| 6,053,905 | A | 4/2000 | Daignault, Jr. et al. | |
| 6,139,540 | A | 10/2000 | Rost et al. | |
| 6,183,420 | B1 | 2/2001 | Douk et al. | |
| 6,254,550 | B1 | 7/2001 | McNamara et al. | |
| 6,409,717 | B1 | 6/2002 | Israelsson et al. | |
| 6,488,637 | B1 * | 12/2002 | Eder et al. | 600/585 |
| 6,569,106 | B1 | 5/2003 | Ullman | |
| 6,588,588 | B2 | 7/2003 | Samuels | |
| 6,602,207 | B1 | 8/2003 | Mam et al. | |
| 6,673,025 | B1 | 1/2004 | Richardson et al. | |
| 7,399,308 | B2 * | 7/2008 | Borillo et al. | 606/200 |
| 7,494,474 | B2 * | 2/2009 | Richardson et al. | 600/585 |
| 7,618,379 | B2 * | 11/2009 | Reynolds et al. | 600/585 |
| 2001/0021831 | A1 | 9/2001 | Fleischhacker et al. | |
| 2002/0072689 | A1 | 6/2002 | Klint | |
| 2002/0087099 | A1 | 7/2002 | Nanis | |
| 2003/0060731 | A1 | 3/2003 | Fleischhacker | |
| 2003/0181828 | A1 * | 9/2003 | Fujimoto et al. | 600/585 |
| 2003/0216668 | A1 | 11/2003 | Howland et al. | |
| 2004/0106878 | A1 | 6/2004 | Skujins | |
| 2004/0167437 | A1 | 8/2004 | Sharrow | |
| 2004/0167442 | A1 | 8/2004 | Shireman et al. | |
| 2005/0038359 | A1 | 2/2005 | Aimi et al. | |
| 2005/0054953 | A1 | 3/2005 | Ryan | |
| 2008/0200839 | A1 * | 8/2008 | Bunch et al. | 600/585 |
| 2008/0228108 | A1 * | 9/2008 | Jalisi | 600/585 |
| 2008/0234605 | A1 * | 9/2008 | Urie | 600/585 |
| 2009/0198153 | A1 * | 8/2009 | Shriver | 600/585 |

FOREIGN PATENT DOCUMENTS

| | | |
|---|---|---|
| JP | 4-108456 | 4/1992 |
| WO | WO 00/10636 | 3/2000 |
| WO | WO 2005/007033 | 1/2005 |
| WO | WO 2006/002199 | 1/2006 |
| WO | WO 2008/100877 | 8/2008 |
| WO | WO 2010/078544 A1 | 7/2010 |

OTHER PUBLICATIONS

Search Report and Written Opinion of the International Searching Authority dated Sep. 3, 2008 for related PCT PCT/US2008/053636.

Invitation to Pay Additional Fes and Where Applicable, Protest Fee from the International Searching Authority dated Jun. 10, 2008 for related PCT US2008/053636.

International Preliminary Report on Patentability dated Aug. 27, 2009 and Written Opinion of the International Searching Authority for related PCT US2008/053636.

International Search Report and Written Opinion of the International Searching Authority dated Mar. 31, 2010 for related PCT US2010/020025.

* cited by examiner

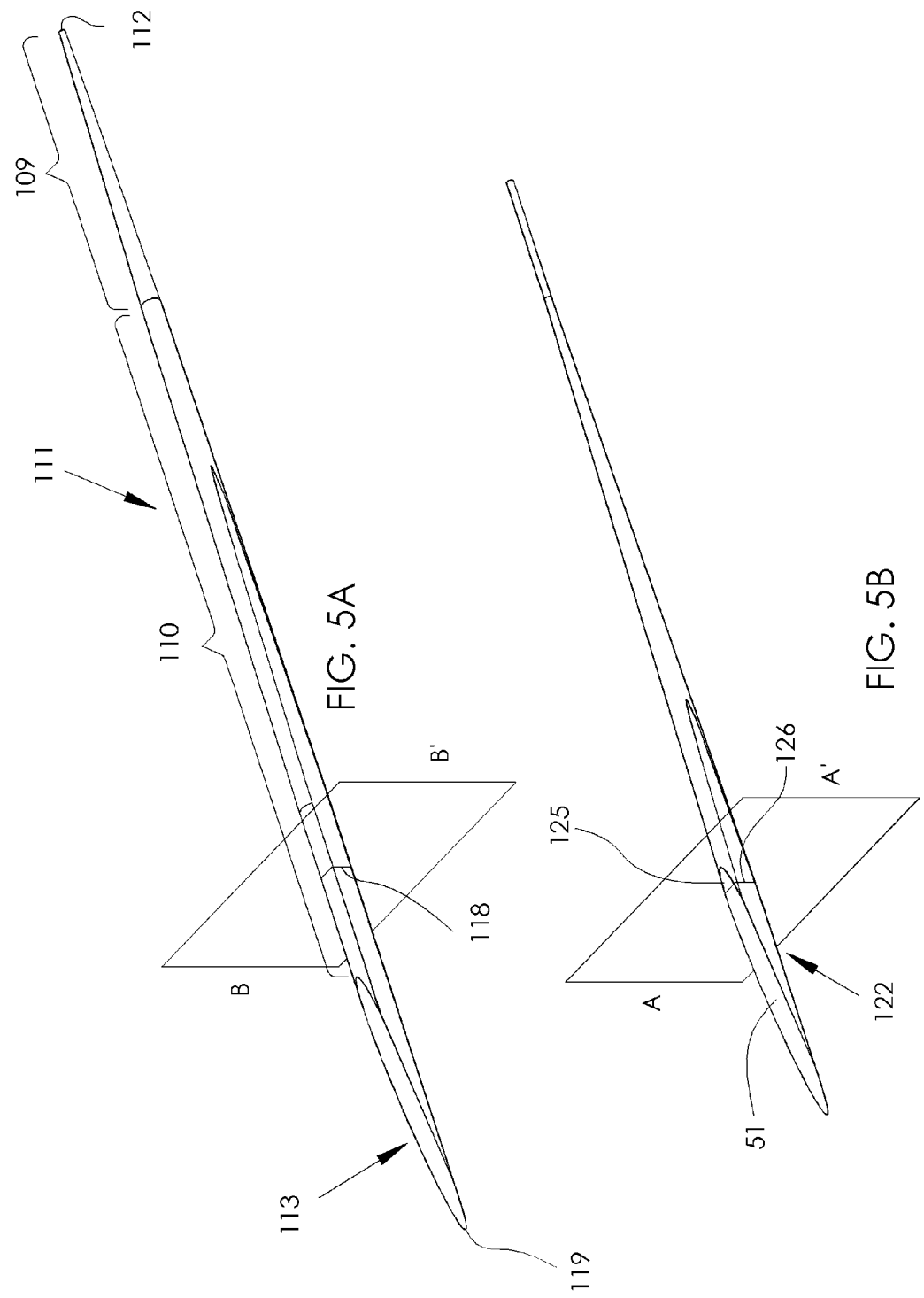

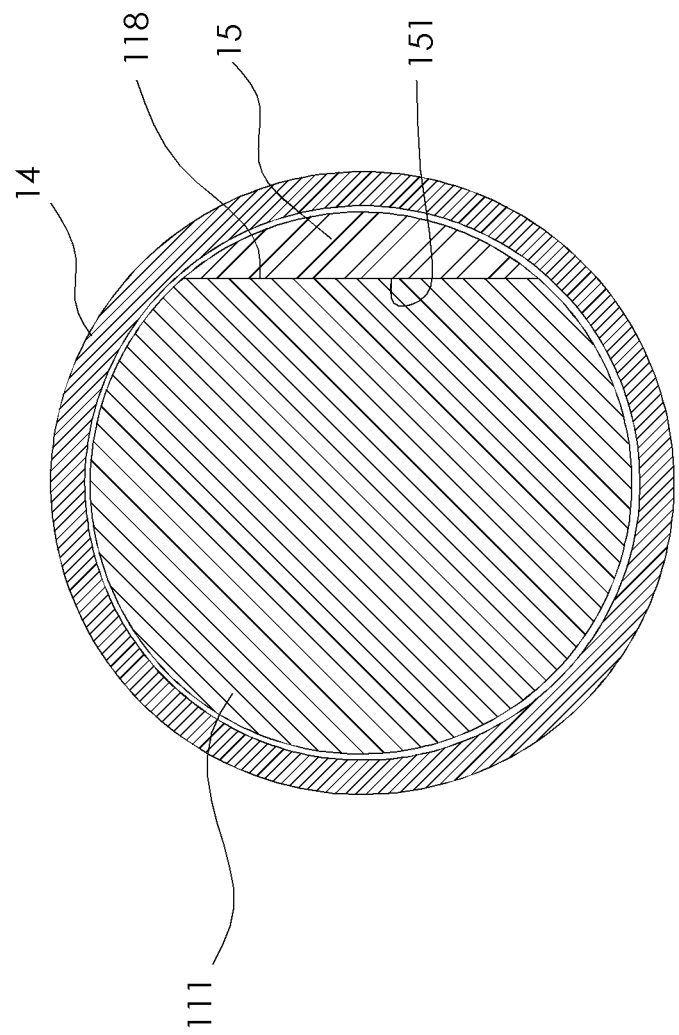

(SECTION A-A')

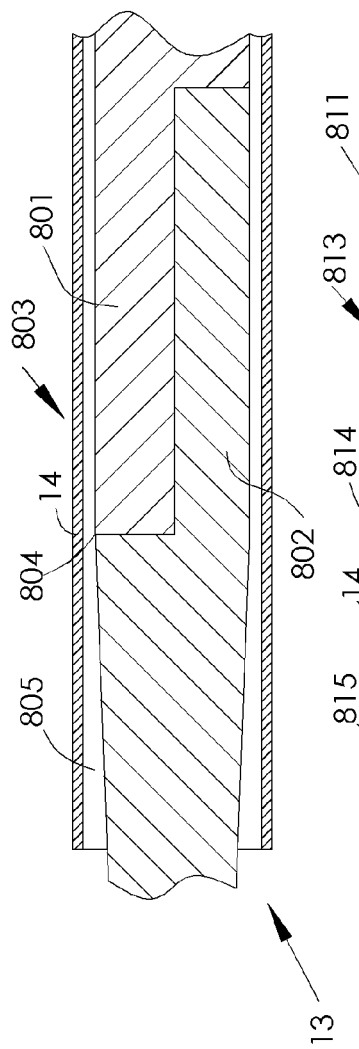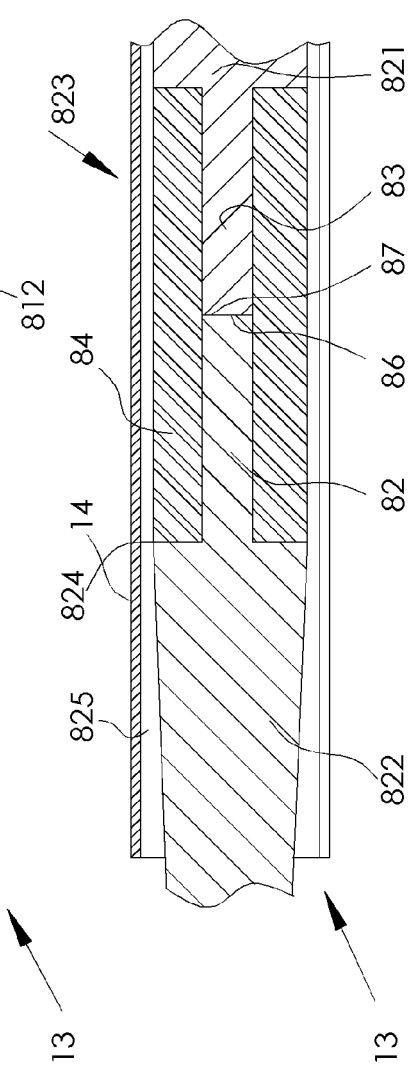

MEDICAL GUIDE WIRE

TECHNICAL FIELD

This application relates to endoscopic and laparoscopic medical devices, and in particular, to guide wires used in endoscopic and laparoscopic procedures.

BACKGROUND

Reviewing scheduling order; reviewing patents and file history Medical guide wires, also known as wire guides, are widely used in cardiovascular surgical procedures as well as gastrointestinal tract, ureter tract and urinary tract procedures to assist the physician in positioning catheters and other devices within the body. In this technique, a physician guides a slim and flexible guide wire through a body lumen until the guide wire enters the body organ or cavity of interest. The typical medical guide wire used for cardiovascular, urological, and other procedures has an elongated body with a distal end and a proximal end. For example, in cardiovascular procedures the distal end of the guide wire is introduced into the vascular system and manipulated from the proximal end by the physician. Once the guide wire has been placed, the physician may then use the guide wire to pass other instruments into the patient. For instance, the proximal end of the guide wire may be placed in a lumen of a catheter or an endoscope, and the catheter or endoscope may then also be guided into the patient along the same guide wire that was previously placed.

To navigate the vascular and other pathways the guide wire must be stiff enough to permit the physician to "push" the wire. However, the guide wire must be flexible enough to be guided to the desired location in the patient not to damage the patients vascular structures. To meet these needs, a variety of wire guides are known having variable flexibility constructions.

For instance, U.S. Pat. Nos. 3,789,841; 4,545,390; and 4,619,274 show guidewires in which the distal end section of the wire is tapered along its length to allow great flexibility in that remote region of the guidewire.

U.S. Pat. No. 4,925,445 suggests the use of a two-portion guidewire having a body portion relatively high in rigidity and a distal end portion which is comparatively flexible.

U.S. Pat. No. 4,991,602 describes a guide wire useful for guiding a catheter within a blood vessel. The guide wire is formed of a single length of shape memory alloy. The guide has a central portion of uniform diameter and substantially identical tapered end portions each terminating in enlarged diameter portions defining smoothly rounded beads which function to reduce trauma to the lumen of a blood vessel.

U.S. Pat. No. 6,488,637B describes a composite guide wire for use in a catheter and for accessing a targeted site in a lumen system of a patient's body. The composite guide wire includes multi-section guide wire assemblies having superelastic distal portions and super-elastic braided reinforcements along the mid or distal sections. A variation of the guide wire includes coating of the wire with a tie layer and then with one or more lubricious polymers to enhance its suitability for use within catheters and within the interior of vascular lumen.

Another wire guide that attempts to combine stiffness with flexibility properties is described in U.S. Pat. No. 6,001,068. The guide wire includes a first wire located at the distal end of the guide wire, a second wire located at the proximal end of the guide wire and having a flexural rigidity greater than that of the first wire, and a tubular connector for joining the first and second wires. The connector has one or more grooves or slits formed on the distal side of the boundary between the first wire and the second wire. The connector is formed of a material different from the material of the first wire. The proximal portion of the first wire is provided with a thin metal coating. The first wire is joined to the connector by brazing at the portion provided with the thin metal coating.

U.S. Pat. No. 6,918,882B describes various designs suitable for connecting different guide wire sections together. More particularly, connecting two portions of a guide wire having different material compositions with a connector having a third composition which is readily weldable to each of the dissimilar portions of the guide-wire. A transition area may be designed to provide a region of desired flexibility characteristics.

SUMMARY

There is a need in the art for, and it would be useful to have a novel medical guide wire, which is capable to be safely introduced into the confined space of the individual cardiovascular, ureter, urinary bladder, or biliary tract, to help the physician to position catheters and other devices within the body.

It would be advantageous to have a guide wire that would have a stiff mid section, sufficient to permit the physician to "push" the wire. The wire guide must have a sufficiently flexible distal section and soft distal tip so as not to injure tissue of the patient's vascular or urinary tracts and other structures, and to bend smoothly when deflected. It would also be useful to have a proximal tip readily soft to prevent scratches of optical parts of the instruments used together with the guide wire. A guide wire should be effectively maneuvered through the vasculature to smoothly transmit torque from the proximal end of the guide wire to the tip of its distal section. It should be noted that in the description and claims that follow, the terms "proximal" and "distal" are used with reference to the operator of the medical guide wire.

Moreover, it would also be advantageous to avoid a discontinuity of stiffness in the joint or connection between the distal section, mid section and the proximal section of the guide wire. When such discontinuity exists, it may lead to stress concentration, difficulty in achieving the desired performance of the guide wire, and could conceivably lead to kinking or failure of the guide wire. Accordingly, what is needed is a wire guide with better continuity between its distal and other sections.

The present disclosure satisfies the aforementioned need by providing a guide wire for guiding a medical device within a body lumen. The guide wire comprises a proximal section, a distal section, and a mid section. The proximal section includes a proximal wire core having proximal and distal ends. The proximal wire core has at least one portion that is tapered with contraction towards the proximal end of the proximal wire core. Likewise, the distal section includes a distal wire core having proximal and distal ends. The distal wire core has at least one portion that is tapered with contraction towards the distal end of the distal wire core (121). The mid section includes a joint configured for joining the distal end of the proximal wire core and the proximal end of the distal wire core.

The guide wire also comprises a safety wire extending along the mid section, and extending along at least a part of the proximal section and a part of the distal section. Moreover, the guide wire comprises an outer tubing for enveloping the overlapping joint and at least parts of the proximal and distal sections.

According to one embodiment, the contraction of the distal wire core is asymmetric with respect to a longitudinal axis of the guide wire.

According to one embodiment, the contraction of the distal wire core starts within the region of the joint. For example, the contraction of the distal wire core can start at a place located between a center of the joint and a tip of the proximal end. According to this embodiment, the mid section includes an empty space defined between the outer surface of the distal wire core and the outer tubing.

The joint for joining the proximal wire core and the distal wire core can be selected from an overlapping scarf joint, an overlapping splice joint, an overlapping tapered joint, an overlapping male-female joint, and a butt joint.

According to one embodiment, the distal section is configured as relatively flexible and floppy section of the guide wire with respect to the portion of the proximal section adjacent to the mid section.

According to one embodiment, the proximal wire core comprises a stainless steel.

According to one embodiment, the distal wire core comprises a superelastic alloy.

According to one embodiment, the distal wire core is formed of a metal alloy including at least one component selected from nickel, titanium, iron, and colastic balt.

According to one embodiment, the outer tubing includes a coiled wire.

According to one embodiment, the outer tubing is coated by a polymer coating.

According to one embodiment, the outer tubing is fixed to the safety wire, the distal wire core, and/or to the distal wire core at least at the mid section.

According to one embodiment, the distal end of the proximal wire core and the proximal end of the distal wire core both include beveled ends.

According to one embodiment, the joint joining the distal wire core and the proximal wire core is a scarf joint in which the distal end of the proximal wire core and the proximal end of the distal wire core are both beveled ends that abut one another without fixation of contacting surfaces of the beveled ends together.

According to one embodiment, a joint angle of the joint defined as an angle between the seam formed by the contacting beveled surfaces of the distal end and the proximal end and the longitudinal axis of the guide wire is in the range of about 0.2 degrees to about 45 degrees.

According to one embodiment, the outer tubing and the safety wire both extend beyond the proximal end of the proximal wire core.

According to another embodiment, the proximal wire core extends along the entire proximal section and terminates together with the outer tubing and the safety wire.

According to one embodiment, at least the distal wire core forming the distal section of the guide wire is coated with a layer of a coating of a lubricious substance.

According to a further embodiment, a hydrophilic coating is applied to an external surface of at least one section of the guide wire, selected from the proximal section, the distal section, and the mid section.

Another representative embodiment provides a guide wire for guiding a medical device within a body lumen. The guide wire includes a proximal section including a proximal wire core with a proximal end and a distal end, the proximal wire core includes at least one tapered portion with contraction towards the proximal end of said proximal wire core. A distal section is provided that includes a distal wire core with a proximal end and a distal end, the distal wire core including at least one tapered portion with contraction towards the distal end of the distal wire core. A mid section is provided that includes a joint that joins said distal end of the proximal wire core and said proximal end of the distal wire core. The wire guide further includes a safety wire that extends along the mid section of the wire guide and extends along at least a portion of the proximal section and at least a portion of the distal section. An outer tubing envelopes said overlapping joint and at least parts of the proximal and distal sections.

Yet another representative embodiment provides a method of forming a wire guide. The method includes forming a first elongate wire core and a second elongate wire core, each wire core comprising a first end portion being tapered with contraction towards a first end of each wire core; and joining an opposite second end portion of each of the first and second elongate wire cores at a joint portion. The method additionally includes placing a safety wire along at least a portion of the first wire core; and enclosing the first and second wire cores with an outer tubing to envelope a joint of the second end portions of the first and second elongate wire cores.

According to one embodiment, the method comprises fixing the safety wire to at least one wire core selected from the first and second wire cores.

According to a further embodiment, the method comprises fixing the outer tubing to the safety wire and to at least one portion of the end portions of the first and second elongate wire cores.

There has thus been outlined, rather broadly, the more important features of the disclosure in order that the detailed description thereof that follows hereinafter may be better understood. Additional details and advantages of the disclosure will be set forth in the detailed description, and in part will be appreciated from the description, or may be learned by practice of the disclosed embodiments.

BRIEF DESCRIPTION OF THE DRAWINGS

In order to understand the detailed description below and to see how it may be carried out in practice, embodiments will now be described, by way of non-limiting example only, with reference to the accompanying drawings, in which:

FIG. 5A illustrates an exemplary prospective view of the proximal wire core of the medical guide wire shown in FIG. 4;

FIG. 5B illustrates an exemplary prospective view of the distal wire core of the medical guide wire shown in FIG. 4;

FIGS. 6A and 6B are schematic transverse cross-sectional views of the medical guide wire of FIG. 4 taken along the line A-A' and B-B', respectively;

FIGS. 8A-8C illustrate schematic longitudinal side cross-sectional views of the joint in the mid portion of the medical guide wire, according to various embodiments.

DETAILED DESCRIPTION OF EMBODIMENTS

Figure 1:
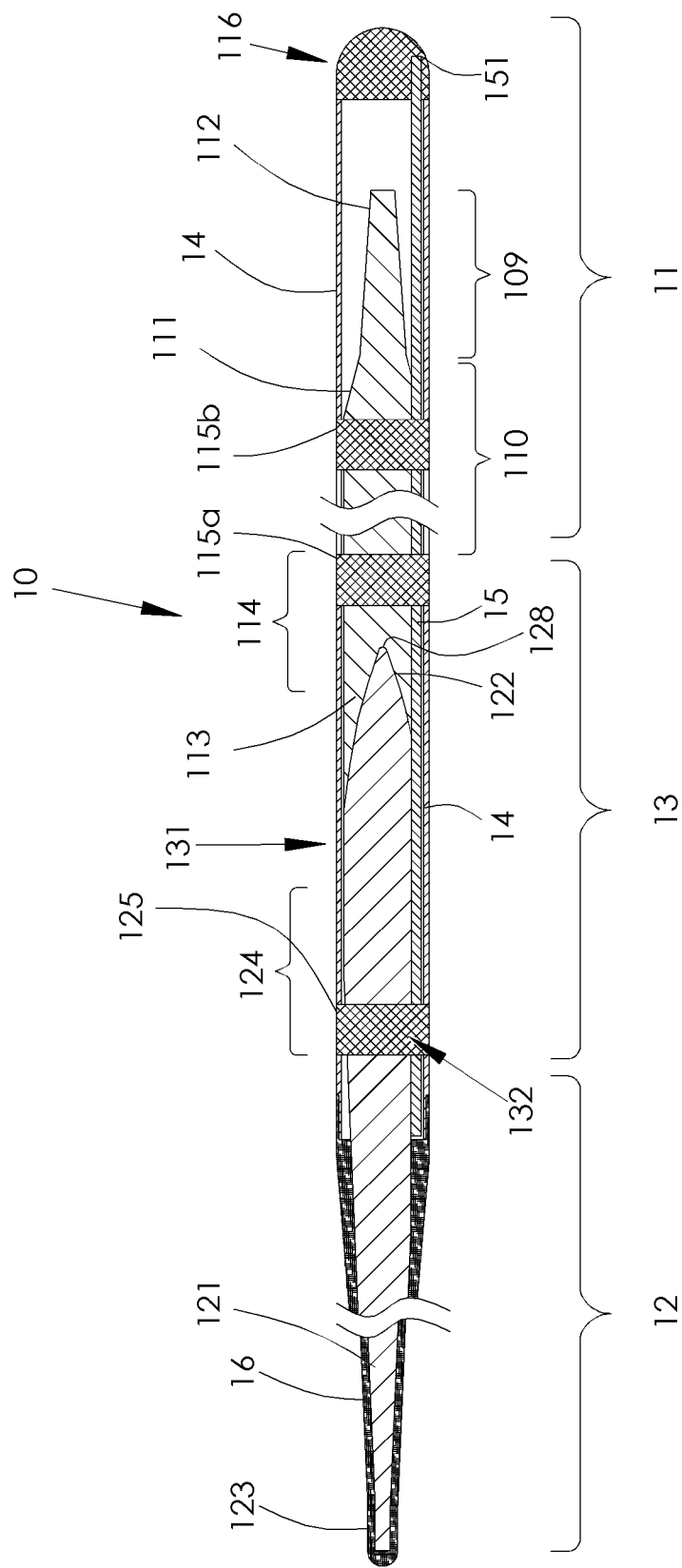
FIG. 1 is a schematic longitudinal top cross-sectional fragmentary view of a medical guide wire, according to one embodiment.

The principles of the design and method for use of the disclosed medical device may be better understood with reference to the drawings and the accompanying description, wherein like reference numerals have been used throughout to designate identical elements. It being understood that these drawings which are not necessarily to scale and proportions, are given for illustrative purposes only and are not intended to limit the scope of the disclosed subject matter or the claims. Examples of constructions, materials, dimensions, and manufacturing processes are provided for selected elements. Those versed in the art should appreciate that many of the examples provided have suitable alternatives which may be utilized.

Referring to FIG. 1 a schematic longitudinal top cross-sectional fragmentary view of a medical guide wire 10 is illustrated, according to one embodiment. It should be understood that the medical guide wire 10 is not bound to the scale and proportion illustrated in FIG. 1 and in other drawings.

Generally, the medical guide wire 10 includes a proximal section 11 and a distal section 12 which are joined or secured together in a mid section 13. The terms "proximal" and "distal" are used herein with reference to the operator of the medical guide wire.

The proximal section 11 includes a proximal wire core 111 having a proximal wire core end 112 and a distal wire core end 113. The distal section 12 includes a distal wire core 121 having a proximal wire core end 122 and a distal wire core end 123. The mid section 13 includes a portion 114 of the proximal wire core 111, a portion 124 of the distal wire core 121, and a joint 131 joining the distal wire core 121 and the proximal wire core 111. In other words, the proximal wire core 111 extends through the proximal section 11, the portion 114 and is joined to the distal wire core 121 within the mid section 13. In turn, the distal wire core 121 extends through the distal section 12, a portion 124 and is joined to the proximal wire core 111 within the mid section 13.

According to the embodiment shown in FIG. 1, the joint 131 is an overlapping joint in which the proximal end 122 of the distal wire core 121 abuts the distal end 113 of the proximal wire core 111, however other embodiments are contemplated. According to the shown embodiment, the proximal end 122 and the distal end 113 are beveled ends, which are connected by a scarf joint. When desired, the joint 131 can be a butt joint, a splice joint or any other suitable joining arrangement. Various types of the connecting ends forming the joint 131 will be described herein below, in accordance with various embodiments.

Preferably, the guide wire 10 has multiple sections of varying flexibility. For example, the proximal end 112 of the proximal wire core 111 and the distal end 123 of the distal wire core 121 can be configured as relatively flexible and floppy sections of the guide wire 10, whereas the major portion of the of the proximal wire core 111 can be more rigid than the proximal end 112 and the distal end 123, to provide pushability and torqueability to the guide wire 10. In turn, the mid section 13 may have varying flexibility in the region of the joint 131.

In general, the proximal wire core 111 and the distal wire core 121 can be made of any suitable materials, and can be made of the same or dissimilar materials. For example, materials such as metals, polymers, and the like can be used as material for the proximal and distal wire cores 111 and 121.

The material used to construct the proximal wire core 111 can be selected to be relatively stiff for pushability and torqueability. In this case, the proximal wire core 111 can be formed of relatively stiff material, such as a stainless steel wire, and the like. However, the proximal wire core 111 may be formed of a more flexible material, for example a metal or metal alloy such as a nickel-titanium alloy (e.g., Nitinol), nickel-chromium alloy, nickel-chromium-iron alloy, cobalt alloy, or other suitable material.

In turn, the material used to construct the distal wire core 121 may be selected, preferably, to be relatively flexible to not injure tissue and to bend smoothly when deflected, however other embodiments are contemplated. Accordingly, the distal wire core 121 may be formed of a relatively flexible material such as a straightened super elastic or linear elastic alloy, for example, a nickel-titanium wire, such as Nitinol. In some embodiments, the nickel-titanium alloy comprises titanium (Ti) at a concentration of from about 48 to about 52 atomic percent, with the remainder being essentially nickel. Alternatively, the distal wire core 121 may comprise a metal or metal alloy such as stainless steel, nickel-chromium alloy, nickel-chromium-iron alloy, cobalt alloy, or other suitable material. When desired, the distal wire core 121 may be made from a radiopaque material required for X-ray imaging of the guide wire 10. Examples of the radiopaque material include, but are not limited to, nickel-titanium alloys alloyed with heavy elements such as gold, platinum, palladium, rhenium and etc.

As shown in FIG. 1, the proximal wire core 111 forming the proximal section 11 in the vicinity of the proximal end 112 has a portion 109 that is continuously tapered with contraction towards the proximal end 112. In turn, the majority of the distal wire core 121 forming the distal section 12 is continuously tapered with contraction towards the distal end 123 of the distal wire core 121, however other embodiments are contemplated. The contractions of the proximal wire core 111 towards the proximal end 112 and contractions of the distal wire core 121 towards the distal end 123 can be either symmetric or asymmetric with respect to the longitudinal axis (not shown) of the guide wire. Places from which the contractions towards the proximal end 112 and the distal end 123 begin may be located either within or outside the joint 131.

The cross-sectional dimension of the tapered portion of the proximal wire core 111 and the tapered distal wire core 121 may decrease along their lengths linearly. However, when desired the cross-sectional dimension of the proximal wire core 111 and the distal wire core 121 may be varied along their lengths non-linearly. These provisions provide additional flexibility to the tapered portion of the proximal section 11 and to the distal section 12. The outer periphery of the proximal wire core 111 and the distal wire core 121 may be formed with a centerless grinding process, laser cutting or by another suitable method to provide a smooth profile, and desired tapers and changes in dimension in the region of the joint 131 and other portions.

Figure 2:
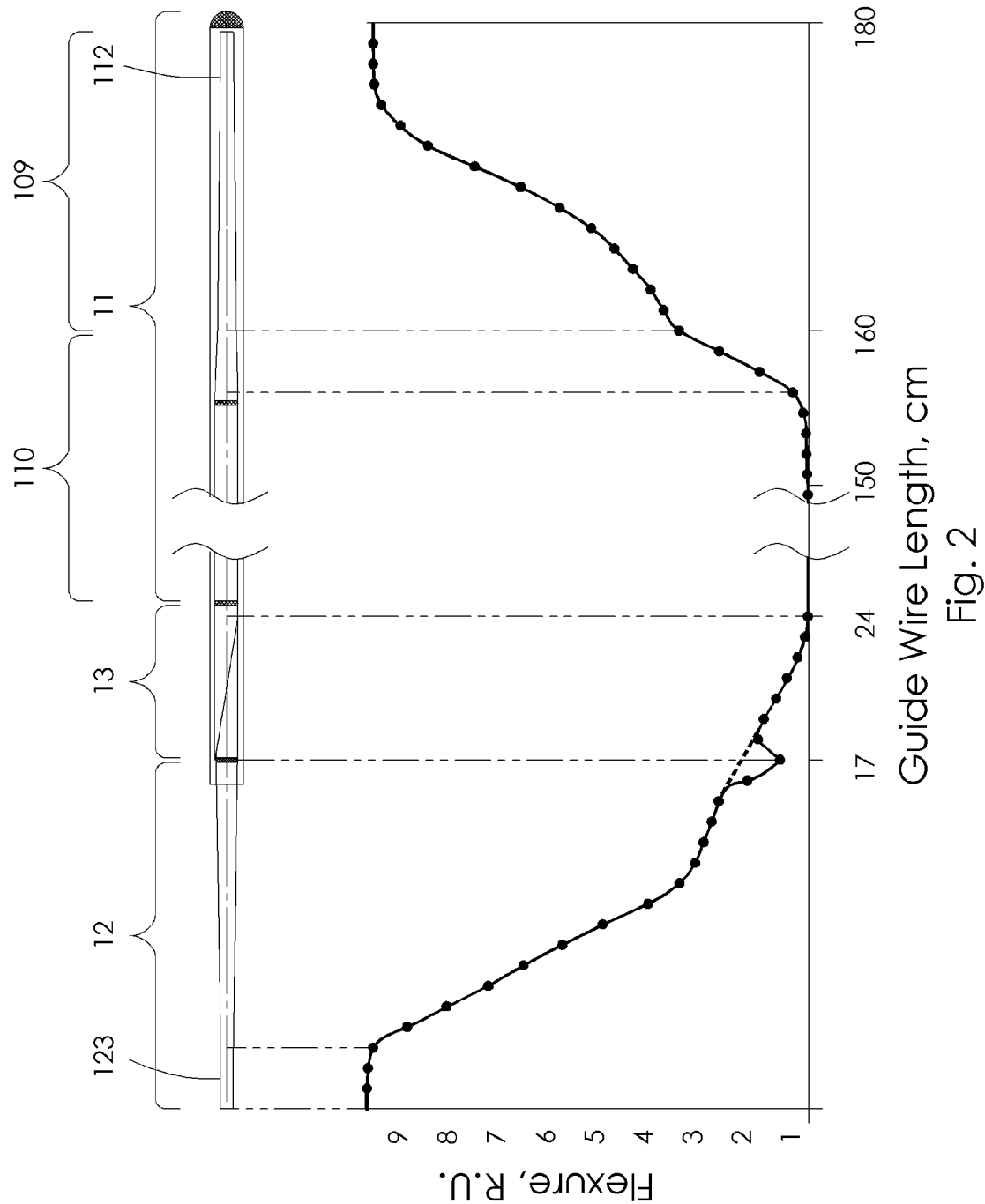
FIG. 2 illustrates an example of a relative flexure of the guide wire of FIG. 1 along the guide wire length.

FIG. 2 illustrates an example of a relative flexure of the guide wire along its length. During the measurements, the guide wire was horizontally fixed sequentially at various places along its length, and for each fixation place the same predetermined weight was applied to the guide wire at a certain distance from the fixation place. The absolute magnitude of the flexure of the guide wire under the weight was recorded and the relative flexure with respect to the magnitude of flexure at the rigid portion 110 of the proximal wire core 111 was calculated. As can be seen in FIG. 2, flexibility of the guide wire changes rather smoothly along the length, and the flexibility at the proximal end 112 and at the distal end 123 has values 10 times greater than the flexibility in the rigid portion 110 of the proximal wire core 111. In the region of the mid section 13 the flexibility changes rather smoothly.

Turning back to FIG. 1, the medical guide wire 10 is further formed by an outer tubing 14 and by a safety wire 15. The outer tubing 14 can envelop the joint 131 and at least portions 114 and 124 of the mid section 13. The outer tubing 14 can, preferably, be formed as a coiled wire, however other embodiments are contemplated. For example, the outer tubing 14 can be formed as a cannula. According to an embodiment, the outer tubing 14 is formed from braided reinforced tubes, such as polyimide or other polymers.

According to an embodiment, the outer tubing 14 can surround the joint 131 and align the majority of the proximal wire core 111, the majority of the safety wire 15 and at least a portion of the distal wire core 121 next to the joint 131 towards the distal end 123.

When the outer tubing 14 is formed as a coiled wire, it can, for example, be made from a length of flat wire or from a length of round or otherwise shaped wire ranging in dimensions to achieve the desired flexibility and other characteristics. Such a wire should be coiled into the flexible outer tubing 14 with a lumen defined therein. The coil could be single or multifilar, and can be wrapped in a helical fashion by conventional winding techniques. The coil may have a relatively loose or relatively tight pitch. For example, the pitch of adjacent turns of coil may be tightly wrapped so that each turn touches the succeeding turn, or the pitch may be set such that coil is wrapped in an open fashion such that spaces are defined between adjacent turns of coil. The pitch along the length of the coil can vary. For example, the pitch may be loose near the proximal end 112 of the proximal wire core 111 to increase proximal flexibility, but may be tight near the mid section 13.

The outer tubing 14 can be made of a variety of materials including metals, metal alloys, polymers, and the like. Some examples of material for use in the outer tubing 14 include, but are not limited to, stainless steel, nickel-chromium alloy, nickel-chromium-iron alloy, cobalt alloy, or other suitable materials. Some additional examples of suitable material include straightened super elastic or linear elastic alloy (e.g., nickel-titanium) wire, or alternatively, a polymer material, such as a high performance polymer. In some embodiments, the outer tubing 14 can be made of radiopaque materials such as gold, platinum, tungsten, or the like, or alloys thereof that may serve to further aid visualization of the guide wire during use.

When desired, the outer tubing 14 can be covered by a coating (not shown) including a hydrophilic layer, in order to reduce the friction coefficient. Examples of the materials suitable for the coating include, but are not limited to, polytetrafluoroethylene (PTFE), Fluorinated ethylene propylene (FEP), Polyethylene terephthalate (PET), etc.

The outer tubing 14 can be fixed to the safety wire 15 and to the distal wire core 121 at the portion 124 of the mid section 13, thereby forming a joint 125. According to a further embodiment, the outer tubing 14 can also be fixed to the safety wire 15 and to the proximal wire core 121 at the portion 114 of the mid section 13, thereby forming a joint 115a. When desired, the outer tubing 14 can also be fixed to the safety wire 15 and to the proximal wire core 121 in a region close to the end 112, thereby forming a joint 115b.

The joints 125, 115a, and 115b can be made with a laser weld, plasma weld pulse, electromagnetic weld or other welding process. Moreover, such fixing may be done by soldering, brazing, crimping, application of glues or by any other known technique depending on the material selected for each component.

The safety wire 15 provides additional strength to the guide wire 10 and allows extraction of the guide wire from the patient's body (not shown) in the case of the abruption of the proximal wire core and/or the outer tubing 14. The safety wire 15 can be made of any suitable material and sized appropriately to give the desired characteristics, such as strength and flexibility characteristics. Some examples of suitable materials include metals, metal alloys, polymers, and the like. In some embodiments, the safety wire 15 may be formed of a metal or metal alloy such as stainless steel, nickel-chromium alloy, nickel-chromium-iron alloy, cobalt alloy, a nickel-titanium alloy, such as a straightened super elastic or linear elastic alloy (e.g., nickel-titanium) wire.

The safety wire 15 can extend towards a physician (not shown) along at least the entire mid section 13. In some embodiments, the safety wire 15 may also extend from the mid portion 13 (proximate to the joint 131) along the entire or at least a part of the proximal section 11 towards a proximal end 116 of the guide wire 10. When desired, the safety wire 15 may also further extend along a part of the distal section 12 towards the distal end 123.

As shown in FIG. 1, the outer tubing 14 and the safety wire 15 both extend beyond the proximal end 112 of the proximal wire core 111, however other embodiments are contemplated. For example, according to the embodiment shown in FIG. 3, the proximal wire core 111 may extend along the entire proximal section 11 and terminate together with the outer tubing 14 and the safety wire 15. The proximal end 151 of the safety wire 15 can be fixed at the proximal end 116 of the guide wire 10 to the outer tubing (coiled wire) 14 and/or to the proximal end 122 of the distal wire core 121. Such fixing may be done by laser welding, plasma welding, pulse electromagnetic welding, soldering, swaging, crimping, application of glues, or by any other known technique.

As shown in FIG. 1, the external surface of the distal wire core 121 forming the distal section 12 of the guide wire 10 is coated with a thin layer 16 of a coating of a lubricious substance to improve its lubricity without adversely affecting the flexibility or shapeability of the guide wire. When desired, the thin layer 16 can extend further toward the proximal end 116 and cover a part or entire external surface of the outer tubing 14. Examples of materials suitable for the layer 16 include, but are not limited to, polymer materials (e.g., polyurethane) that provide a relatively low coefficient of friction and a smooth and atraumatic external surface. In other embodiments, the layer 16 may be made of Teflon.

In other embodiments, a hydrophilic coating (not shown) can be applied to the external surface of one or more sections of the guide wire 10. Examples of materials suitable for the hydrophilic coating of the guide wire 10 include, but are not limited to, polyarylene oxides, polyvinylpyrolidones, polyvinylalcohols, hydroxy alkyl cellulosics, algins, saccharides, caprolactones, and the like, and mixtures and combinations thereof.

Figure 4:
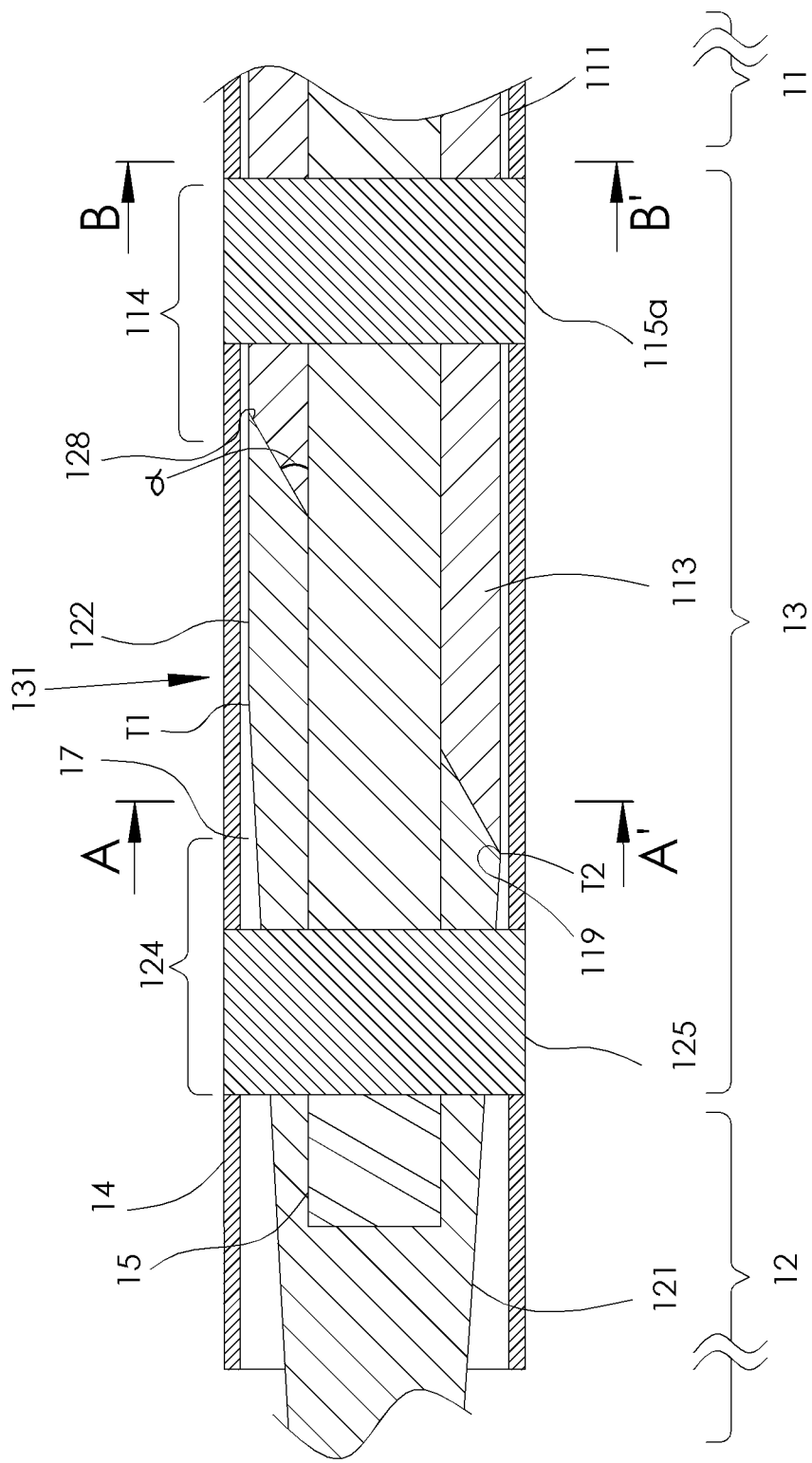
FIG. 4 illustrates a schematic longitudinal side cross-sectional view of the mid portion of the medical guide wire shown in FIG. 1.

FIG. 4 illustrates a schematic longitudinal side cross-sectional view of the mid portion 13 of the medical guide wire shown in FIG. 1, according to one embodiment. The proximal end 122 of the distal wire core 121 and the distal end 113 of the proximal wire core 111 are both beveled ends which overlap one another. Thus, as shown in FIG. 4, the overlapping joint 131 is a scarf joint.

According to one embodiment, in the scarf joint the beveled ends abut one another without fixing the contacting surfaces together. In such a case, as described above, the distal wire core 121 and the proximal wire core 111 are fixed to the outer tubing 14 at the joints 125 and 115a proximate the region of the scarf joint.

In other embodiments, the contacting surfaces of the beveled ends can be welded, soldered, or glued to each other. Because the flexibility characteristics of the distal wire core 121 and the proximal wire core 111 are different, the scarf joint can form a flexibility transition region that has a relative flexibility that is between the flexibility of the proximal wire core 111 and the flexibility of the distal wire core 121 (see also FIG. 2).

The outer diameter of the distal wire core 121 and the proximal wire core 111 in the vicinity of the joint 131 can, for example, be in the range of about 0.2 mm to about 1.5 mm, whereas the length of the beveled ends forming the joint 131 can, for example, be in the range of about 2 mm to about 15 cm, and is preferably in the range of about 4 cm to about 10 cm. For these cases, the joint angle α defined as an angle between the seam formed by the surfaces of the beveled ends 113 and 122 and a longitudinal axis (not shown) of the guide wire 10 can be in the range of about 0.2 degrees to about 45 degrees. The relatively large overlap of the connecting wire core ends 113 and 122 can ensure smooth bending properties of the guide wire along the mid section 13.

As described above, the distal wire core 121 is continuously tapered with contraction towards the distal end 123 of the distal wire core 121. The contraction can be either symmetric or asymmetric with respect to the longitudinal axis (not shown) of the guide wire 10. According to the embodiment shown in FIG. 4, the contraction of the distal wire core 121 is asymmetric and it starts within the region of the joint 131, however other embodiments are contemplated. According to this embodiment, a place T1 from which the contraction of the distal wire core 121 towards its distal end 123 is located within the region of the joint 131. The place T1 can, for example, be located at the center of the joint 131 or even more close to a tip 128 of the proximal end 122. The contraction of the distal wire core 121 on the diametrically opposite side with respect to the longitudinal axis (i.e., a place T2) starts from a tip 119 of the distal end 113.

Figure 9:
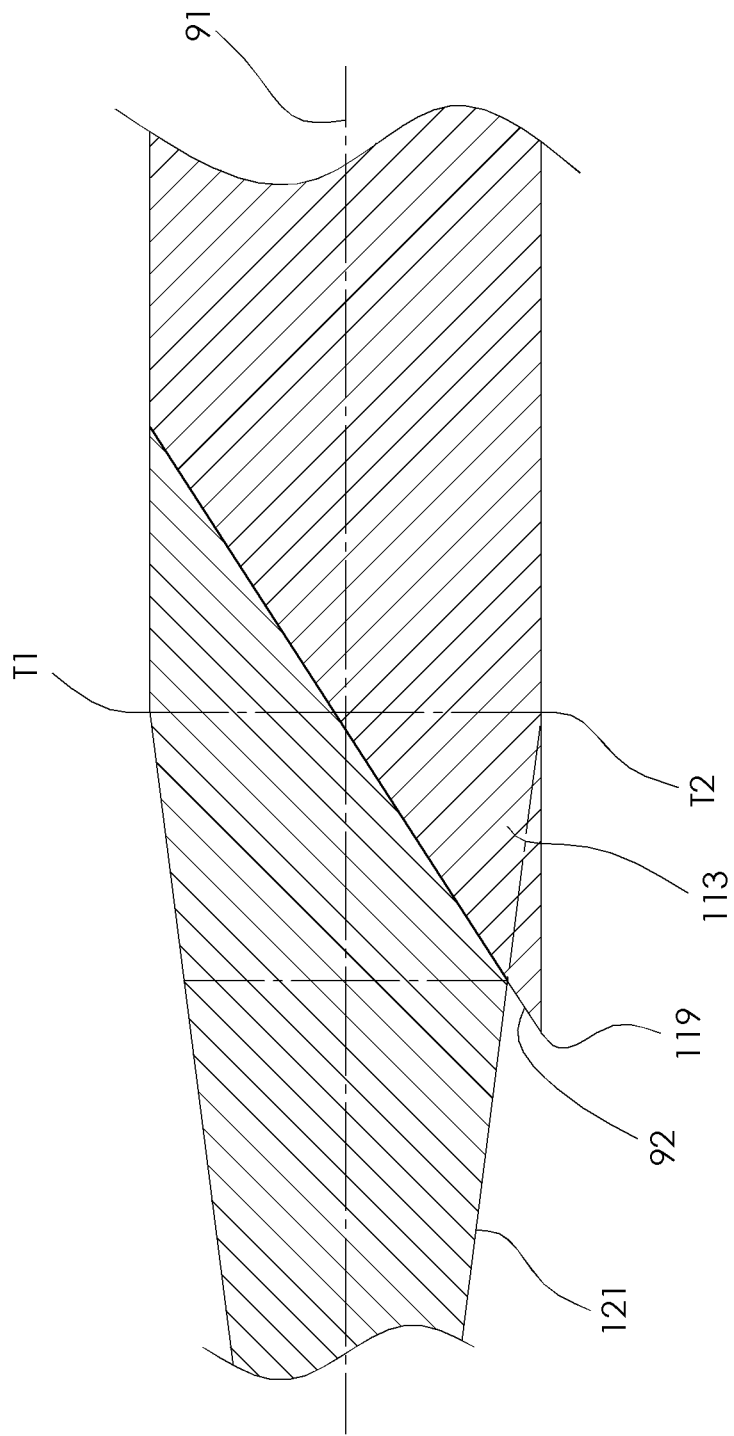
FIG. 9 illustrates a joint of the distal wire core and the proximal wire core according to yet an embodiment.

When desired, the place T2 can also be located within the joint 131. FIG. 9 shows an embodiment according to which the contraction of the distal wire core 121 is symmetrical with respect to a longitudinal axis 91. In this case, the tip 119 of the distal end 113 is projected away from the surface of distal wire core 121 and forms a tooth 92.

Turning back to FIG. 4, the mid section 13 includes an empty volume 17 defined between the outer surface of the distal wire core 121 and the inner surface of the outer tubing 14. This provision provides additional flexibility of the guide wire 10 in the region of the mid section 13 and in the surrounding regions.

FIG. 5A illustrates a prospective view of the proximal wire core 111 of the medical guide wire shown in FIG. 4. FIG. 6A illustrates a schematic cross-sectional view of the medical guide wire of FIG. 4 taken along the lines B-B'.

Referring to FIG. 5A and FIG. 6A together, the cross-section of the proximal wire core 111 along B-B' is formed in a "D" shape, with a flat portion 118 that extends along a chord formed upon the wire, however other embodiments are contemplated. The remaining circumference of the proximal wire core 111 includes a circular orientation.

As shown in FIG. 6A, the safety wire 15 may be formed in a "D" shape similar to the "D" shape of the proximal wire core 111. The cross-section of the safety wire 15 includes a flat portion 151 that extends along a chord formed upon the wire and the remaining circumference of the safety wire 15 forming a circular orientation. As described above, the safety wire 15 is parallel with and contacts the proximal wire core 111 along at least the majority of the length of the proximal wire core 111. Specifically, the flat portion 118 of the proximal wire core 111 is aligned with the flat portion 151 of the safety wire 15 to make surface-to-surface contact therebetween. The safety wire 15 aligns the proximal wire core 111 within the guide wire 10 and additionally provides alignment for the outer tubing (e.g., coiled wire) 14 surrounding the proximal wire core 111, as discussed hereinabove.

FIG. 5B illustrates an exemplary prospective view of the distal wire core 121 of the medical guide wire shown in FIG. 4. For the possibility to see a surface 51 of the beveled end 122, the distal wire core 121 is shown by turned clockwise by 180 degrees with respect to the view of the shown in FIG. 4.

Figure 6B:
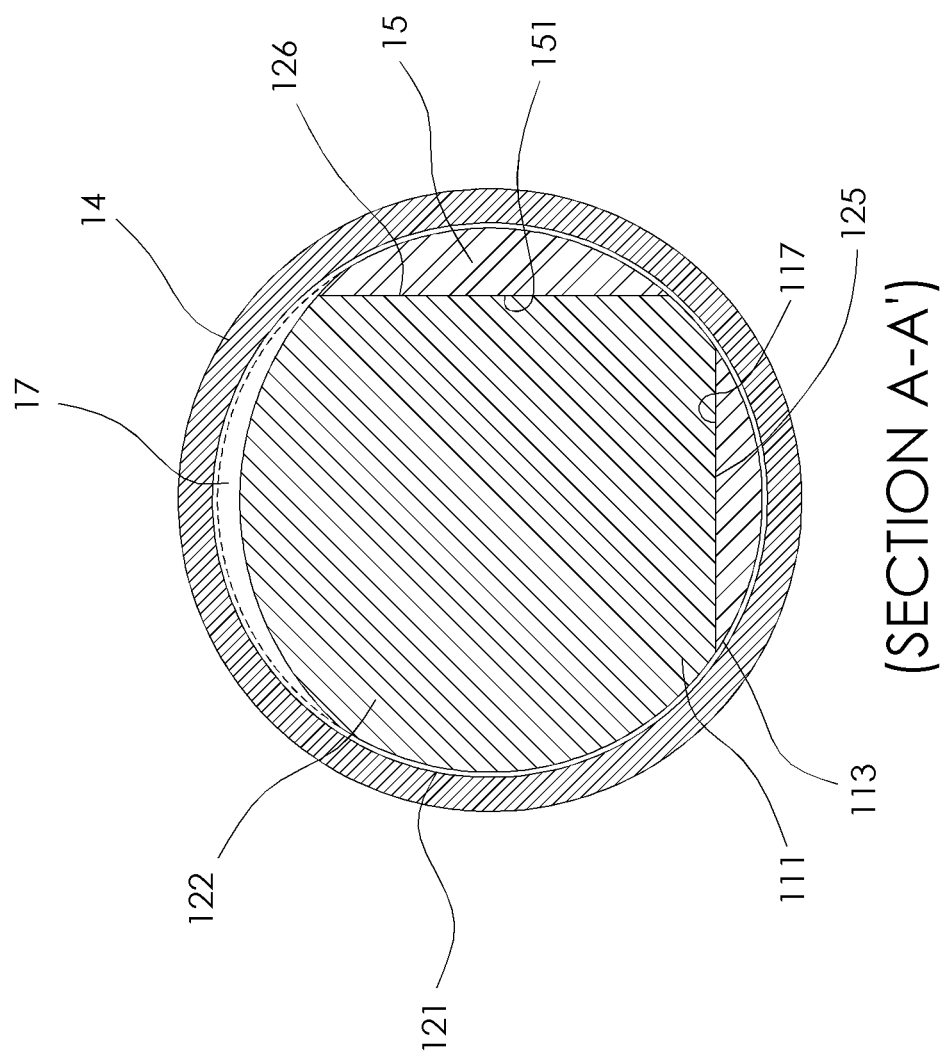

FIG. 6B illustrates a schematic cross-sectional view of the medical guide wire of FIG. 4 taken along the lines A-A'. As shown in FIG. 6B, the cross-section of the distal end 113 of the proximal wire core 111 has mainly a "D" shape. It includes a flat portion 117 that extends along a chord formed upon the wire and a remaining circumference of the proximal wire core 111. The cross-section of the safety wire 15 is similar to that shown in FIG. 6A, and includes a flat portion 151 that extends along a chord formed upon the wire and the remaining circumference of the safety wire 15 forming a circular orientation.

Referring to FIG. 5B and FIG. 6B together, the cross-section of the proximal end 122 of the distal wire core 121 has two flat sections 125 and 126. The flat sections 125 can be aligned with the flat portion 117 of the proximal wire core 111 to make surface-to-surface contact of the scarf joint 131, whereas the flat section 126 is aligned with the flat portion 151 of the safety wire 15 to make surface-to-surface contact between the distal wire core 121 and the safety wire 15.

Figures 7A, 7B, 7C, 7D, 7E, 7F:
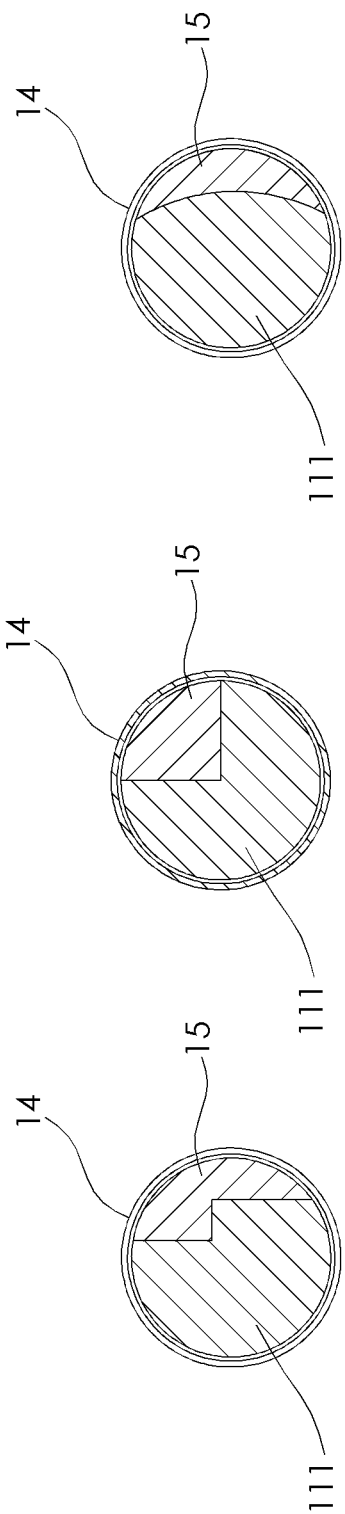
FIGS. 7A-7F illustrate schematic transverse cross-sectional views of the medical guide wire taken along the line B-B', according to various embodiments.

Referring to FIGS. 7A-7F, schematic transverse cross-sectional views of the medical guide wire taken along the lines B-B', respectively, are illustrated, according to various embodiments. Specifically, FIG. 7A shows a step profile of the cross-sectional cut of the guide wire between the proximal wire core 111 arranged in surface-to-surface contact with the safety wire 15. Further, FIG. 7B and FIG. 7C show a sector-type and crescent-type profiles of the cross-sectional cut of the guide wire, correspondingly. FIG. 7D shows a profile of the cross-sectional cut of the guide wire in which the proximal wire core 111 has mainly a "D" shape, whereas the safety wire 15 has a trapezoid shape. FIG. 7E corresponds to the embodiment shown in FIG. 5B. FIG. 7F shows a profile of the cross-sectional cut of the guide wire in which the proximal wire core 111 has mainly a round shape with a rectangular groove accommodating a safety wire 15 having a rectangular shape.

Figure 3:
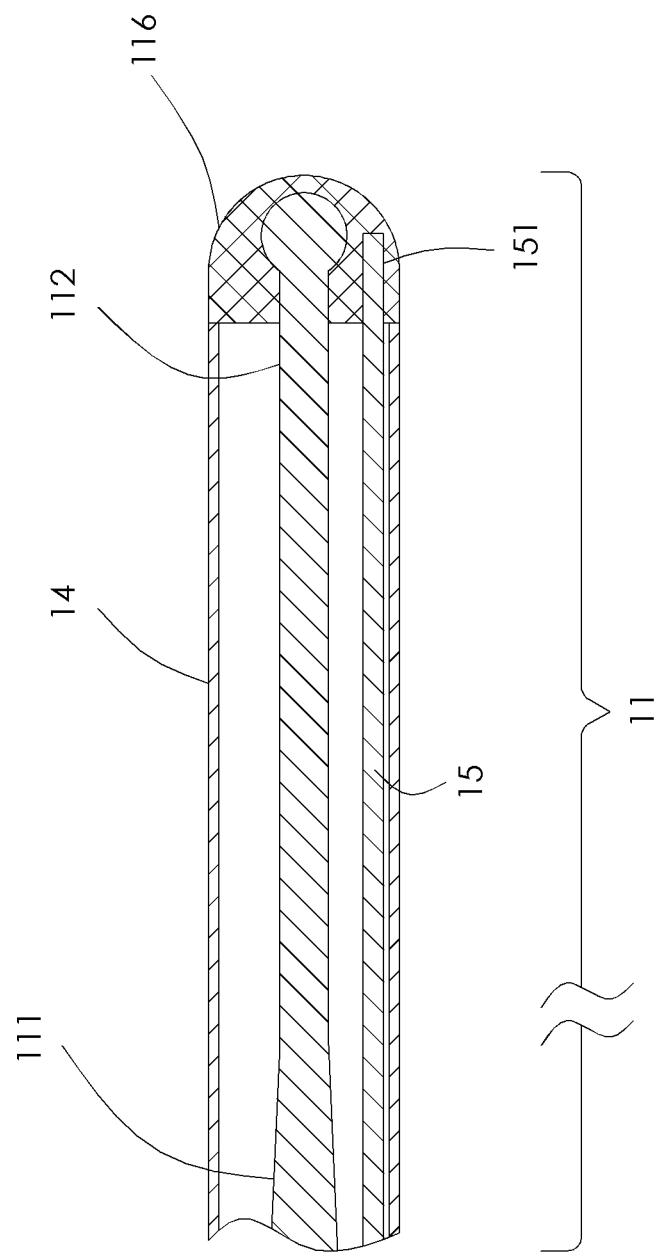
FIG. 3 illustrates a schematic enlarged top cross-sectional view of a portion of the proximal portion of a wire guide, according to another embodiment.

It should be understood that the joint between the proximal wire core and the distal wire core may be not only an overlapping scarf joint, as shown in FIG. 1 and FIG. 3, but also an overlapping half lap splice joint, an overlapping tapered joint, an overlapping male-female joint, or any other suitable joining arrangement. FIGS. 8A-8C illustrate schematic longitudinal side cross-sectional views of the joint in the mid section 13 of the medical guide wire, according to various embodiments.

Referring to FIGS. 8A, the joined ends of the proximal wire core 801 and the distal wire core 802 are overlapped and form a half lap splice joint 803. The joint 803 is surrounded by an outer tubing 14. The distal wire core 802 is tapered with contraction towards the distal end (not shown). The contraction can be either symmetric or asymmetric with respect to the longitudinal axis (not shown) of the guide wire. According to the embodiment shown in FIG. 8A, the contraction is symmetric and it starts in the region of the joint 803, however other embodiments are contemplated. A place 804 from which the contraction of the wire guide begins is located at the end of the splice of the proximal wire core 801, i.e. at the distal end of the region of the joint 803. It should be understood that when desired, the place from which the contraction of the wire guide begins could also be within or outside the joint 803. According to the provision shown in FIG. 8A, the mid section 13 includes an empty space 805 defined between the outer surface of the distal wire core 802 and the outer tubing 14. This provision provides additional flexibility of the guide wire in the region of the mid section 13.

As shown in FIG. 8B, the joined ends of the proximal wire core 811 and the distal wire core 812 are overlapped and form a male-female joint 813. The joint 813 is surrounded by an outer tubing 14. The distal wire core 812 is tapered with contraction towards the distal end (not shown). The contraction can be either symmetric or asymmetric with respect to the longitudinal axis (not shown) of the guide wire. According to the embodiment shown in FIG. 8B, the contraction is symmetric and it starts in the region of the joint 813, however other embodiments are contemplated. A place 814 from which the contraction of the wire guide begins is located at the end of the proximal wire core 811, i.e. at the distal end of the region of the joint 813. It should be understood that when desired, the place from which the contraction of the wire guide begins can also be within or outside the joint 813. According to the provision shown in FIG. 8B, the mid section 13 includes an empty space 815 defined between the outer surface of the distal wire core 812 and the outer tubing 14. This provision provides additional flexibility of the guide wire in the region of the mid section 13.

As shown in FIG. 8C, the joined ends of the proximal wire core 821 and the distal wire core 822 are connected by means of a butt joint 823 that is formed by two connecting ends 82 and 83 which are formed at the distal end of the proximal wire core 821 and the proximal end of the distal wire core 822, respectively. During fabrication, the distal and proximal connecting ends 82 and 83 are trimmed for decreasing their diameter and then inserted into a flexible sleeve 84 from opposing directions such that the two butt surfaces 86 and 87 face each other. Once the ends 82 and 83 are positioned inside the flexible sleeve 84, the assembly may then be secured together using an anaerobic adhesive or solder, or any other bonding material that meets design and strength requirements, such as epoxies, glues, adhesive, laser welding, spot welding, or other suitable technique.

The distal wire core 822 is tapered with contraction towards the distal end (not shown). The contraction towards the distal end can be either symmetric or asymmetric with respect to the longitudinal axis (not shown) of the guide wire. According to the embodiment shown in FIG. 8C, the contraction is symmetric and it starts in the region of the joint 823, however other embodiments are contemplated. A place 824 from which the contraction of the wire guide begins is located at the end of flexible sleeve 84, i.e. at the distal end of the region of the joint 813. It should be understood that when desired, the place from which the contraction of the wire guide begins can also be within or outside the joint 823. According to the provision shown in FIG. 8C, the mid section 13 includes an empty space 825 defined between the outer surface of the distal wire core 822 and the outer tubing 14. This provision provides additional flexibility of the guide wire in the region of the mid section 13.

As such, those skilled in the art can appreciate that while the present invention has been described in terms of preferred embodiments, the concept upon which this disclosure is based may readily be utilized as a basis for the designing of other structures and processes for carrying out the several purposes of the present disclosure.

Although FIGS. 1, 5A show the guide wire in which the diameter of the proximal section 11 in the region 109 and 5B continuously decreases towards the proximal end 112, and FIGS. 1, 5B show the guide wire in which the diameter of the distal section 12 continuously decreases towards the distal end 123, when desired, the proximal section 11 and the distal section 12 can have a number of tapered sections of different diameters.

As shown in FIGS. 5A, 5B and 7A through 7F, the proximal section 11 and the distal section 12 have solid cross-sections. However, in some embodiments, one or both section 11 and section 12 can have a hollow cross-section. In yet other embodiments, the proximal section 11 and the distal section 12 can each include a combination of sections or portions having solid cross-sections and hollow cross sections.

Although set forth with specific reference to guide wires in the exemplary embodiments shown in the figures and discussed below, the disclosure may be applicable to almost any medical device having an elongated structure made up of two or more adjacent or consecutive elongated members or sections that are connected together. For example, the disclosure may be applicable to elongated shafts, for example hypotube shafts and the like, for intravascular catheters (e.g., guide catheters, diagnostic catheters, rapid exchange balloon catheters, stent delivery catheters, etc.) or drive shafts for intravascular devices (atherectomy catheters, IVUS catheters, intravascular rotational devices, etc.), and the like, or other such medical devices.

It should be understood that the disclosed medical device is not limited to medical treatment of a human body. It can be successfully employed for medical treatments of animals as well.

Also, it is to be understood that the phraseology and terminology employed herein are for the purpose of description and should not be regarded as limiting.

It is important, therefore, that the scope of the disclosure is not construed as being limited by the illustrative embodiments set forth herein. Other variations are possible within the scope of the present disclosure as defined in the appended claims. Other combinations and sub-combinations of features, functions, elements, and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

The invention claimed is:

1. A guide wire (10) for guiding a medical device within a body lumen, comprising:
   a proximal section (11) including a proximal wire core (111) formed of a first material and having a proximal end (112) and a distal end (113), said proximal wire core (111) having at least one portion (109) being tapered with contraction towards the proximal end (112) of said proximal wire core (111);
   a distal section (12) including a distal wire core (121) formed of a second material and having a proximal end (122) and a distal end (123), said distal wire core (121) having at least one portion being tapered with contraction towards the distal end (123) of said distal wire core (121);

a mid section (13) including a joint (131) joining said distal end (113) of the proximal wire core (111) and said proximal end (122) of the distal wire core (121);

a continuous safety wire (15) extending along the mid section (13), and at least a portion of the proximal section (11) and the distal section (12); and an outer tubing (14) enveloping said joint (131) and at least parts of the proximal section (11) and the distal sections (12);

wherein in the mid section (13), the proximal wire core (111), the distal wire core (121), and the safety wire (15) in combination form a generally circular cross section of the combined materials of the proximal wire core (111), the distal wire core (121), and the safety wire (15).

2. The guide wire of claim 1, wherein said contraction of said distal wire core (121) is asymmetric with respect to a longitudinal axis of the guide wire (10).

3. The guide wire of claim 1, wherein said contraction of said distal wire core (121) starts within the region of or proximate the joint (131).

4. The guide wire of claim 1, wherein said contraction of said distal wire core (121) starts between a center of the joint and a tip (128) of said proximal end (122).

5. The guide wire of claim 2, wherein the mid section (13) includes an empty volume (17) defined between the outer surface of the distal wire core (121) and an inner surface of the outer tubing (14).

6. The guide wire of claim 4, wherein the joint (131) is selected from an overlapping scarf joint, an overlapping splice joint, an overlapping tapered joint, an overlapping male-female joint, and a butt joint.

7. The guide wire of claim 1, wherein the distal section (12) is more flexible than a portion of the proximal section (11) adjacent to the mid section (13).

8. The guide wire of claim 1, wherein the proximal wire core (111) comprises stainless steel.

9. The guide wire of claim 1, wherein the distal wire core (121) comprises a superelastic alloy.

10. The guide wire of claim 1, wherein the distal wire core (121) is formed of a metal alloy including at least one component selected from nickel, titanium, iron, and cobalt.

11. The guide wire of claim 1, wherein the distal wire core (121) is formed of a nickel-titanium alloy comprising titanium at a concentration of about 48 to about 52 atomic percent, with the remainder being essentially nickel.

12. The guide wire of claim 1, wherein the outer tubing (14) comprises a coiled wire.

13. The guide wire of claim 1, wherein the outer tubing (14) is fixed to the safety wire (15) and at least one of the distal wire core (121) or the proximal wire core (111) at the mid section (13) thereof.

14. The guide wire of claim 1, wherein said distal end (113) of the proximal wire core (111) and said proximal end (122) of the distal wire core (121) each comprise beveled ends.

15. The guide wire of claim 14, wherein the joint (131) is a scarf joint in which the beveled end of said distal end (113) of the proximal wire core (111) and the beveled end of said proximal end (122) of the distal wire core (121) abut one another without fixation together.

16. The guide wire of claim 14, wherein a joint angle defined between a seam formed by the abutted beveled ends of the distal end (113) and said proximal end (122) and a longitudinal axis of the guide wire (10) is in the range of about 0.2 to about 45 degrees.

17. The guide wire of claim 1, wherein the outer tubing (14) and the safety wire (15) both extend beyond the proximal end (112) of the proximal wire core (111).

18. The guide wire of claim 17, wherein a proximal end portion of the outer tubing is fixably retained to a proximal end portion of the safety wire.

19. The guide wire of claim 1, wherein the safety wire is fixed to the outer tubing at one or more locations within the mid section.

20. The guide wire of claim 17, where the safety wire is fixed to the distal wire core at the mid section.

21. The guide wire of claim 17, wherein the safety wire is fixed to the proximal wire core at the mid section.

22. The guide wire of claim 1, wherein the proximal wire core (111) extends along the entire proximal section (11) and terminates together with the outer tubing (14) and the safety wire (15).

23. The guide wire of claim 1, wherein at least the distal wire core (121) disposed within the distal section (12) of the guide wire (10) is coated with a layer (16) of a lubricious substance.

24. The guide wire of claim 1, wherein a hydrophilic coating is applied to an external surface of at least one section of the guide wire (10), selected from said proximal section (11), said distal section (12), and said mid section (13).

25. The guide wire of claim 1, wherein the proximal wire core includes a flat portion and the safety wire includes a flat portion, wherein the respective flat portions of the proximal wire and safety wire makes surface-to-surface contact.

26. The guide wire of claim 20, wherein the distal wire core includes a flat portion, wherein the flat portion of the distal wire core and the flat portion of the safety wire makes surface-to-surface contact.

* * * * *